(12) United States Patent
Scott

(10) Patent No.: US 6,297,382 B1
(45) Date of Patent: Oct. 2, 2001

(54) COMPOUND AND PROCESS FOR PRODUCING β-ADRENERGIC RECEPTOR AGONIST

(75) Inventor: Robert W. Scott, Mystic, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 09/620,042

(22) Filed: Jul. 20, 2000

Related U.S. Application Data
(60) Provisional application No. 60/145,417, filed on Jul. 23, 1999.

(51) Int. Cl.[7] ............................... C07D 401/04
(52) U.S. Cl. ............................... 546/276.4
(58) Field of Search ............................... 546/276.4

(56) References Cited

U.S. PATENT DOCUMENTS

| | | | |
|---|---|---|---|
| 5,019,578 | 5/1991 | Fisher et al. | 514/275 |
| 5,030,640 | 7/1991 | Fisher et al. | 514/339 |
| 5,977,124 | 11/1999 | Dow | 514/272 |

FOREIGN PATENT DOCUMENTS

| | | | |
|---|---|---|---|
| 0994105 | 4/2000 | (EP) | C07D/213/73 |
| WO9635671 | 11/1996 | (WO) | C07D/213/73 |
| WO9710195 | 3/1997 | (WO) | C07C/45/00 |
| 98/21184 | * 5/1998 | (WO) | . |
| WO9932475 | 7/1999 | (WO) | C07D/311/58 |

OTHER PUBLICATIONS

J. Org. Chem. 1985, 50, pp. 5446–5448.
Tetrahedron Letters, vol. 34, No. 5. pp 785–788, 1993.
Quallich, et al, Letters, Synlett, 1993, pp 929–930.
Quallich et al., Tetrahedron Letters, vol. 34., No. 26, pp 4145–4148, 1993.

Bruekelman, Stephen P., et al. *Protection of Primary Amines as N–Substituted 2,5–Dimethylpyrroles* (1984) Dyson Perrings Laboratory, Oxford University, South Parks Road, Oxford, OX13OY.
Lowe, John A. III et al, *A New Class of Selective and Potent Inhibitors of Neuronal Nitric Oxide Synthase* (1999)Central Research Division, Pfizer Inc. Groton, CT 06340, U.S.A., Central Research Division, Pfier Inc., Sandwich, Kent, England.

* cited by examiner

*Primary Examiner*—Jane C. Oswecki
*Assistant Examiner*—Sonya Wright
(74) *Attorney, Agent, or Firm*—Peter C. Richardson; Gregg C. Benson; Michelle A. Sherwood

(57) ABSTRACT

A process is provided for preparing a compound of the formula:

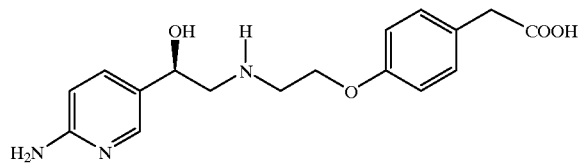

comprising deprotecting a compound of the formula

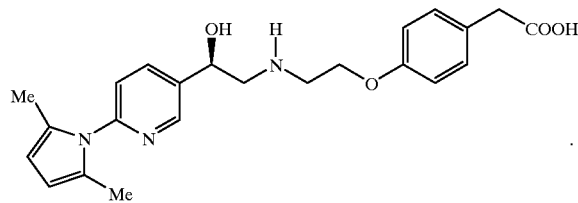

2 Claims, No Drawings

COMPOUND AND PROCESS FOR PRODUCING β-ADRENERGIC RECEPTOR AGONIST

This application is filed claiming priority from co-pending Provisional Application No. 60/145,417 filed Jul. 23, 1999.

FIELD OF THE INVENTION

This invention relates to producing a process for making (4-(2-(2-(6-aminopyridin-3-yl)-2(R)-hydroxyethylamino) ethoxy)phenylacetic acid.

BACKGROUND OF THE INVENTION (4-(2-(2-(6-arinopyddin3-yl)-2(R)-ydroxyethylarino) ethoxy)phenylacebc acid (herein also referred to as "Compound I") has the following structure:

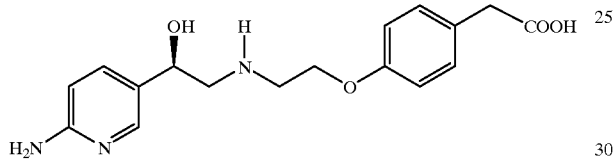

A specific synthesis for compound I is disclosed in Example 1 of International Patent Application PCT/IB95/0344, published internationally as WO 96/356713 which designated, inter alia, the United States, which was filed in the U.S. as copending application Ser. No. 08/1945,551 on Nov. 4, 1997 and which is herein incorporated by reference.

The compound is a selective β-adrenergic receptor agonist which has utility for, inter alia, the treatment of hyperglycemia, obesity, intestinal motility disorders, depression, prostate disease, dyslipidemia, and airway inflammatory disorders such as asthma and obstructive lung disease. The compound is also useful for increasing lean meat deposition and/or improving the lean meat to fat ratio in edible animals such as ungulate animals and poultry. The majority of agonist activity resides in the R-enantiomer.

SUMMARY OF THE INVENTION

This invention provides a process for preparing a compound of the formula:

(I)

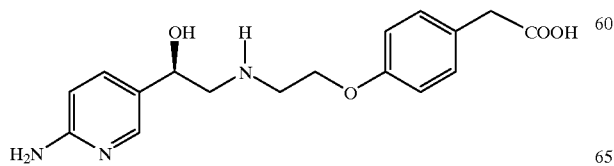

comprising deprotecting a compound of the formula (II)

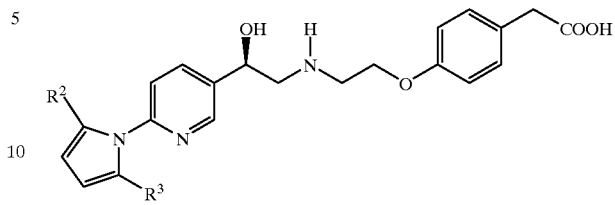

wherein $R^2$ and $R^3$ are independently $C_1$–$C_3$ alkyl or phenyl. Deprotecting in this instance thus means converting the pynolidino group to free amino. As indicated, $R^2$ and $R^3$ can be different. It is preferred that $R^2$ and $R^3$ are the same.

The invention further provides a process for preparing a compound of formula III:

(III)

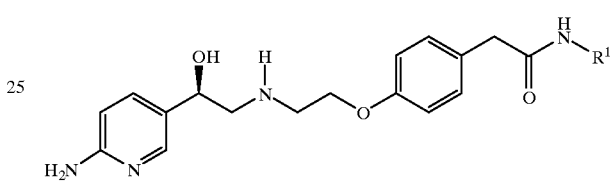

wherein $R^1$ is $C_1$–$C_8$ alkyl, comprising converting the pyrrolidino group in a compound of formula

IV

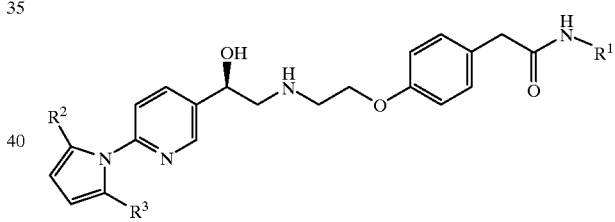

wherein $R^2$ and $R^3$ are as previously defined, to an amino (—$NH_2$) group. It is noted that compound IIII is useful as a penultimate intermediate which can be hydrolyzed by base in a reaction inert solvent to make compound (I).

In another aspect this invention provides a process for preparing a compound of formula I, comprising deprotecting a compound having the formula

IV

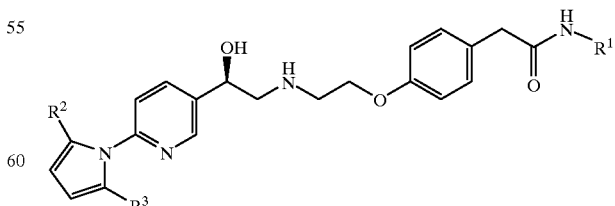

wherein $R^1$, $R^2$, and $R^3$ are is as previously defined. Deprotecting in this instance means converting the western end of the molecule from pyrrolidino to amino, and converting the eastern (amide) portion, (e.g., by hydrolysis) to the free acid.

In further aspects, as further disclosed and described below, this invention provides certain intermediates useful in the processes described above.

DETAILED DESCRIPTION

The chemistry of the instant invention is disclosed as a flow chart in Scheme 1.

conventional drying agent Workup can be by isolation of the product under reduced pressure followed by cleanup with a water/isopropyl ether extraction system, with product being isolated, if desired, by evaporation to yield an oil that solidifies.

Bromide (10) can be converted to 5-(2-haloacety)-2-(2,5-dimethylpyrrol-1-yl)pyndine (15), wherein X, the halo group, is chloro or bromo, by lithium-halogen exchange of

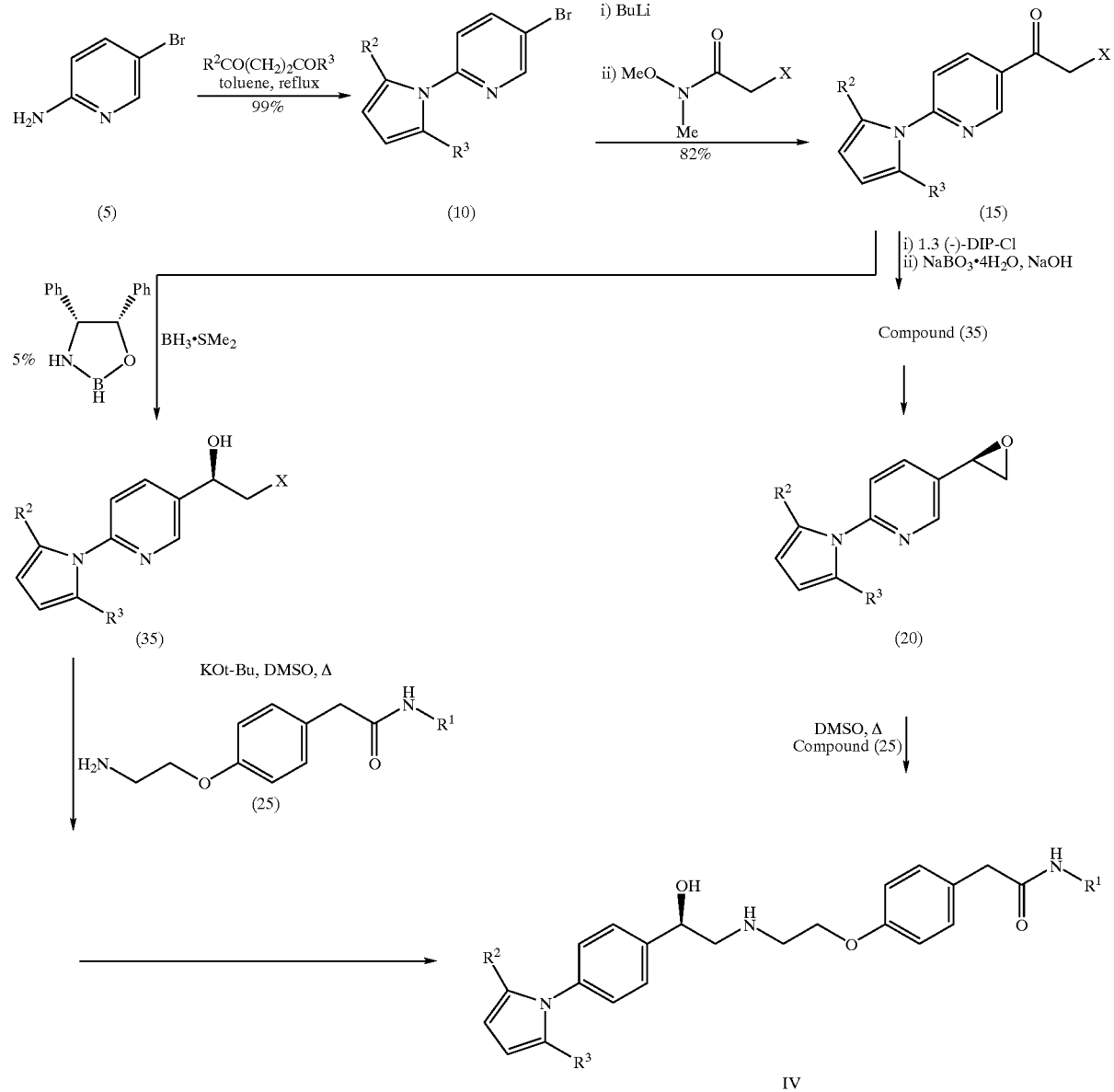

As illustrated, 2-amino-5-bromopyridine (5), available commercially from a number of suppliers including Aldrich Chemical Company, Inc., Milwaukee, Wis., is treated with a compound of the formula $R^2CO(CH_2)_2COR^3$, wherein $R^2$ and $R^3$ are as previously defined, under Dean-Stark conditions to make a 5-bromro-(2,5-dialkyl-pyrrol-1-yl)-pyridine (10), such as 5-bromo-(2,5-dimethylpyrrol-1-yl)-pyridine (10). The reaction conducted in any conventional reaction inert solvent, which allows water removal by distillation, such as toluene or ethylbenzene, or by contacting with a the bromide using butyllithium followed by acylation. Bromide (10) can be treated with butyllithium at reduced temperature, for example −78° C., followed by acylation with the corresponding 2-halo-methoxy-N-methylacetamide or α-halodimethylacetamide while maintaining reduced temperature, to yield α-haloketone (15). The reaction is conducted In a suitable solvent, such as diisopropyl ether, diethyl ether, or preferably, methyl tert-butyl ether (MTBE). The α-haloketone (15) product can be worked up conventionally, for example using aqueous (e.g, 1M) hydrochloric acid, followed by separation of the phases and isolation of (15) by evaporation.

α-haloketone (15) can be used to introduce chirality into the molecule by asymmetrically reducing (15) to the corresponding chiral alcohol (35) [structure shown in left hand pathway] with a chiral pinene-derived boron reagent such as (−)-β-chlorodiisopinocampheylborane (DIP-CI) or with alpine borane, with DIP-CI being preferred. The reaction can be run at reduced temperature in a solvent such as methyl tert-butyl ether or, preferably, THF. Oxidative workup of the intermediate chiral alcohol to afford epoxide (20), without isolating alcohol (35), can be effected by any of several oxidizing agents in the presence of base, including any of hydrogen peroxide, triethylamine Noxide, sodium percarbonate or sodium perborate in the presence of an alkali metal hydroxide such as sodium hydroxide. Sodium percarbonate and sodium perborate are preferred.

Epoxide (20) can be reacted with compound (25) [structure shown in left hand pathway], an alkyl 4-(2-aminoethoxy)phenylacetamide wherein $R^1$ is $C_1$–$C_8$ alkyl, to form the protected intermediate (IV). A crude solution of the epoxide, generated as described above, and the amide (25) can be combined in DMSO and heated to within the range of 60 to 100° C., typically for a timespan of several hours. The product can be worked up by any convenient liquid-liquid extraction procedure (e.g. EtOAc/water) and can be further purified by acid/base extraction. The product can be isolated conventionally by concentration of solvent, for example by evaporation.

A preferred alternative procedure for preparing protected intermediate (IV) involves making α-haloketone (15) as described above and conducting the chemistry alternatively illustrated (left hand pathway) in Scheme 1. Chirality is introduced via an asymmetric reduction of (15), thereby producing chiral alcohol (35), by treating ketone (15) with a catalytic amount of oxazaborolidine as shown, made in situ by combining (1S,2R)-2-amino-1,2-diphenylethanol with $BH^3 \cdot ^{500 \ SMe}_2$ in a solvent such as THF or toluene. Alcohol (35) can then be epoxidized by adding base to the reaction medium to produce epoxide (20) (not shown), which can then be reacted directly with intermediate amide (25) to produce protected alcohol (IV). Epoxide (20), not shown in the left synthesis branch of Scheme 1, was not isolated. Generally a solvent such as DMSO or THF is employed and the reaction medium is heated to a temperature between 60 and 100° C., typically 80–90° C.

Those skilled in the art will appreciate that the asymmetric chiral reduction of α-chloroketone (15) can be conducted using a number of additional chiral reductants, other than those specifically disclosed and illustrated, which are known and/or commercially available.

The preparation of amide (25) has been described in International Patent Publication Number WO 98/21184, herein incorporated by reference, and such compounds are disclosed therein as compounds of formula XVI. Such compounds may be prepared as set forth in the Examples below. For example, the amide of formula (25) wherein $R^4$ is methyl is prepared as set forth in Preparation I below. Other such $C_1$–$C_8$ alkyl amides (25) may be prepared by methods analogous thereto.

The final product, compound I, is made as shown in Scheme 2, by deprotection of compound (IV).

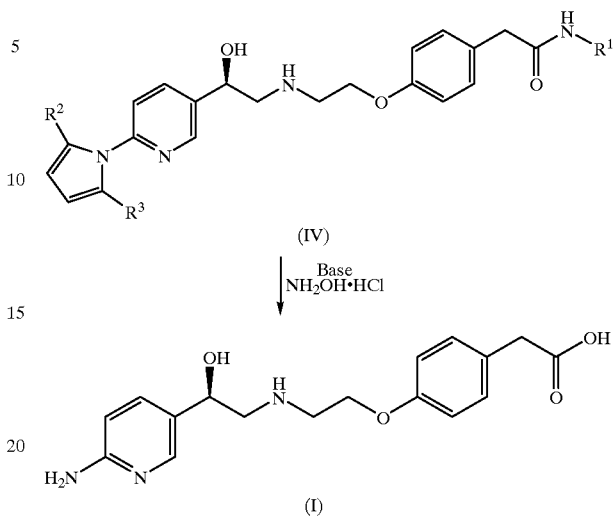

SCHEME 2

The compound (IV) is treated with a base, preferably an alkali metal hydroxide, and with hydroxylamine hydrochloride to deprotect at both the eastern and western ends of the molecule. Thus alcohol (IV) can proceed through compound II or compound III enroute to forming the desired final product. The particular sequence of deprotecton is not considered critical. Alcohol (IV) can first be treated with base to hydrolyze the eastern (amide) portion of the molecule to produce penultimate intermediate II.

Alternatively, alcohol (IV) can first be deprotected at the western end of the molecule by converting the pyrrolidino group to free amino, thereby producing penultimate intermediate III. The final product, compound I, can be isolated in a conventional manner by neutralizing the basic solution and precipitating the zwitterion. Depending on the level of inorganic salts in the material, it may be necessary to rework the product. This can be effected by rebasicifying in aqueous NaOH, filtering, neutralizing to precipitate zwitterion, and repulping in water or a lower alcohol, preferably ethyl alcohol.

Conventional methods and techniques of purification and separation known to those skilled in the art may be used to isolate the compounds of this invention. Such techniques include all types of chromatography, including but not limited to high performance liquid chromatography, column chromatography using common adsorbents such as silica gel, thin layer chromatography and the like; recrystallization; and differential (i.e., liquidliquid) extraction techniques.

In the reaction schemes discussed herein, compounds (II), (IV), (10), (15), (20), and (35) are believed to be novel, and each is presented as an additional novel feature of the invention.

The invention is further disclosed and described by the following examples, which are for purposes of illustration only, not limitation. Reference to "HPLC" means reverse phase HPLC using a Symmetry™ C8 column (Waters Corporation, Milford, Mass.) with an isocratic solvent consisting of various proportions, depending on the analyte, of acetonitrile and pH 3.2 phosphoric acidttriethylamine buffer, using UV detection. The following conventional abbreviations have been employed herein: h—hours; m.p.—melting point; MTBE—methyl tert-butyl ether, IPE—isopropyl ether; N—normal; M—molar, mol—moles; mL—milliliter, g—grams; THF—tetrahydrofuran; temp.—temperature; HPLC—high performance liquid chromatography; rt—room temperature; DMSO—dimethylsulfoxide; EtOAc—ethyl acetate; Me—methyl; Bu—butyl; Ph-phenyl; MeOH—methanol; EtOH—ethanol; NEt$_3$—triethylamine;

EXAMPLE 1

5-Bromo-2-(2,5-dimethylpyrrol-1-yl)-pyridine

To a soluton of 2-amino5bromopyddine (89.87 g, 0.5194 mol) in toluene (500 mL) was added 2,5-hexanedione (85.0 mL, 0.724 mol). The reaction flask was equipped with a Dean-Stark apparatus and the solution heated to reflux for 14 h. The cooled reaction solution was extracted with H$_2$O (2×200 mL). The organic layer was added directly to a plug of SiO$_2$ 3"1×2" w and eluted with toluene (250 mL). This treatment removes a significant amount of color from the crude product. The resulting eluent was concentrated to a right amber oil, which solidified upon cooling to provide 128.76 g (99%) of the title compound.

$^1$H NMR(400 MHz, CDCl$_3$): 2.13 (s, 6), 5.90 (s, 2), 7.12 (d, 1, J=8.3), 7.93 (dd, 1, J=2.5, 8.3), 8.65 (d, J=2.5). $^{13}$C NMR (100 MHz, CDCl$_3$): 13.21, 107.41, 118.92, 123.01, 128.60, 140.51, 150.43, 150.71. Anal.Calcd for C$_{11}$H$_{11}$N$_2$Br: C,52.61; H,4.42; N, 11.16. Found: C,52.68; H,4.28; N, 10.99.

EXAMPLE 2

5-(2-Chloroacetyl)-2-(2,5dimethylpyrrol-1-yl)-pyridine

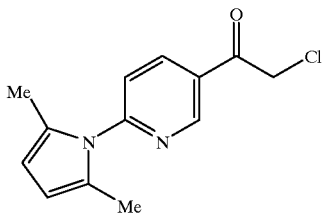

A soluton of the compound made as in Example 1 (100.00 g, 0.3982 mol) in MTBE (1.5 L) was cooled to −78° C. To the solution was added BuLi (175 mL, 2.5 M in hexanes, 0.4375 mol) over 15 min, causing a rise in internal temperature from −78° C. to −70° C. After 10 minutes, a solution of 2-chloro-N-methoxy-N-methylacetamide (63.10 g, 0.4587 mol) in MTBE (200 mL) was added over 10 min, causing a rise in internal temperature from −78° C. to −65° C. After an additional 20 min, 1M HCI (1 L) was added, and the cooling bath removed. The mixture was stirred vigorously for 2 h while warming to rt, and then the layers separated. The aq. layer was extacted with MTBE (400 mL), and the combined organic layers were extracted with 400 mL brine (containing 30 mL 12.5M NaOH-this wash serves to free base any protonated pyridine). The org. layer was dried with MgSO$_4$, filtered and concentrated to provide crude title compound as a red oil. To the crude oil was added hexanes (500 mL) and the mixture stirred vigorously overnight The miture thus obtained was filtered, and the solids rinsed with hexanes (2×100 mL) to provide 81.32 g (82%) of the tite compound as a tan, slightly sticky powder. This material should be stored cold, as prolonged storage at rt will cause darkening and impurity buildup.

$^1$H NMR (300 MHz, CDCl$_3$): 2.18(s, 6), 4.69 (s, 2), 5.93(s, 2), 7.33 (ap. d, 1, J=8.3), 8.36 (ddd, 1, J=1.3, 2.6, 8.5), 9.11–9.13 (m, 1). $^{13}$C NMR (100 MHz, CDCl13): 13.65, 45.48, 108.59, 121.16, 127.70, 128.88, 138.07, 149.78, 155.67, 189.41. Anal. Calcd for C$_{13}$H$_{13}$N$_2$OCl: C, 62.78; H, 5.27; N, 11.26. Found: C, 62.75; H, 5.11; N, 11.27. Mass Spec: AP+=249.1, AP−=247.2.

EXAMPLE 3

(R)-2-(2,5-dimethylpyrrol-1-yl)-5-oxiranylpyridine

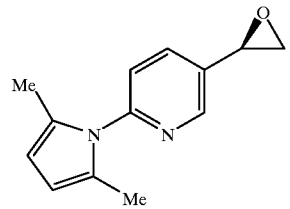

To a N2 purged flask was added (−)-DIP-Cl [(−)-β-chlorodiisopino-campheylborane, 75.90 g, 0.2366 mol which was rinsed into the flask with MTBE (50 mL). To the solution was added THF (112.5 mL), and the mixture cooled to approx. −30 ° C. A solution of compound made as in Example 2 (45.0g, 0.181 mol) in THF (67.5 mL) was added dropwise over 10 min, causing the internal temp. to reach a maximum of −19° C. The reaction was held between −30° C. and −23° C. for 6 h, upon which HPLC analysis showed complete conversion to (R)-5-(2-chloro-1-hydroxyethyl)-2-(2,5-dimethylpyrrol-1-yl)-5-(2chloro-1-hydroxyethyl) pyridine (chiral HPLC of aliquot shows 93% ee). To the solution was added NaBO$_3$•4H$_2$O(27.8 g, 0.181 mol) followed by MTBE (175 mL). The mixture was stirred at rt overnight. To the reaction mixture was added 2N NaOH (675 mL) and the mixture stirred at rt for 6 h. HPLC analysis showed complete conversion of the chiral alcohol to the title epoxide. The layers were separated, and the aqueous layer extracted with MTBE (560 mL). The combined organic layers were extacted with 1N NaOH (225 mL) and brine (225 mL). The organic solution was dried (MgSO4), filtered, and concentrated to a thick oil to provide 82.9 g of crude epoxide which was contaminated with large amounts of pinene derived material. The crude material was used in Example 4 without further purification.

$^1$H NMR (400 MHz, CDCl$_3$): 2.11 (s, 6), 2.90 (dd, 1, J=2.6, 5.3), 3.24 (dd, 1, J=4.0, 5.3), 3.96 (dd, 1, J=2.5, 4.0), 5.89 (s, 2), 7.20 (d, 1, J=8.1), 7.66 (dd, 1, J=2,5, 8.3), 8.56 (d, 1, J=2.5).

EXAMPLE 4

N-methyl (4-(2-(2-(6-(2.5-dimethylpyrrol-1-yl)pyiridin-3-yl)-2(R)-hydroxyethylamino)ethoxy)phen-1-yl)acetamide

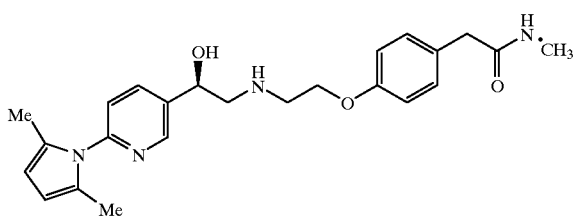

To a crude solution of epoxide produced as in Example 3 (74.6 g mixture, synthesized from 0.163 mol of the ketone produced as in Example 2) in DMSO (140 mL) was added Methyl 4-(2-aminoethoxy)phenylacetamide (68.35 g, 0.3282 mol). The mixture was heated in an 85° C. bath for 8.5 h. Heating was discontinued, and the solution allowed to cool and stir at rt overnight. The mixture was added to 0.5 M HCl (2.8 L), which caused a gum to separate out. The solution was extracted with diethylether (3×1 L) and the ether washes discarded. The aqueous layer was decanted from the gum that settled out, and 1M NaOH (2.1 L) was added. The aq. layer was extracted with EtOAc (2×1.4 L), the combined organic layers extracted with brine (500 mL) and dried over $K_2CO_3$. The solution was filtered and concentrated to an oil, which solidified to a tacky solid upon storage to provide 43.38 g (63% yield, calculated on the crude bromide (10) of Example 1 which was treated as in Examples 2 and 3 without purfication) of title compound which was sufficiently pure to carry forward in the synthesis. A small portion was purified by $SiO_2$ chromatography (MeOH/EtOAc/$NEt_3$) to provide an analytically pure sample.

$^1$H NMR (300 MHz, $CDCl_3$): 2.14 (s, 6), 2.77 (d, 3, J=4.8), 2.84 (dd, 1, J=9.5, 12.2), 3.07 -3.21(m, 3), 3.54(s, 2), 4.13 (t, 2, J=5.0), 4.84 (dd, 1, J=3.3, 9.3), 5.47 (br s, 1), 5.92 (s, 2), 6.93 (d, 2, J=8.7), 7.20(d, 2, J=8.7), 7.24 (d, 1, J=8.1), 7.91 (dd, 1, J=2.3, 8.1), 8.60 (d, 1, J=2.2). $^{13}$C NMR (100 MHz, $CDCl_3$): 13.15, 26.46, 42.70, 48.34, 56.69,67.36, 69.37, 106.87, 114.96, 121.67, 127.34, 128.59, 130.67, 135.76, 136.68, 147.22, 151.36, 157.96, 172.06. Anal. Calcd for $C_{24}H_{30}N_4O_3$: C, 68.22; H, 7.16; N, 13.26. Found: C, 67.82; H, 7.39; N, 13.03.

EXAMPLE 5

(4(2-(2-(6-aminopyiridin-3yl)-2(R)hydroxyethylamino)ethoxy)-phenylacetic acid

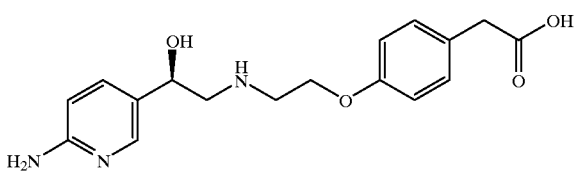

In a 200 mL flask, 40 mL abs. EtOH was added to the compound produced as in Example 4 (11.01 g, 26.06 mmol). The solution was heated up to 70° C. until all the solids had dissolved (30 min). To the solution was added 1.6M NaOH (50 mL), and the bath temperature was raised to 100° C. After 44 hours, HPLC analysis showed only 1.2% starting material remaining. The solution was concentrated to ½ volume by continued heating at 100° C. without condenser, followed by concentration of the remainder under reduced pressure (bath temp=50° C.) to a fluid brown oil. The crude residue was taken up in abs. EtOH (100 mL) and heated to 80° C. To the hot solution was added hydroxlyamine hydrochloride (9.06 g, 0.130 mol) and heating continuted overnight. After a total heating time of 17.5 h, the solution was cooled to rt. The heterogenous solution was filtered, and the solids rinsed with EtOH (25 mL) to provide 9.97 g of crude title compound. To the crude material was added H2O (50 mL) and NaOH (1.72 g) causing most of the solids to dissolve. The solution was heated up to 75° C. for 20 min, and the solution filtered through a scintered glass frit while hot to remove a very small quantity of insoluble sediment. The solution was cooled to rt, and 6M HCl was added dropwise to reduce the pH to ~7, after which stirring was continued for 30 min (note: solids began to come out of solution at pH=9.8). The solids were filtered and rinsed with water (2×10–15 mL). The purified title compound was air dried followed by drying under high vacuum to provide 4.58 g (53%) of product which was pure by HPLC and $^1$H NMR analysis.

EXAMPLE 6

(R)-5-(2-chloro-1-hydroxyethyl)-2-(2,5dimethylpyrrol-1-yl)-5-(2-chloro-1-hydroxyethyl)pyridine

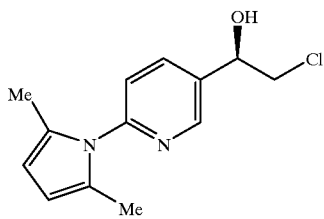

To a solution of (1S,2R)-2-amino-1,2-diphenylethanol (0.2429 g, 1.139 mmol) in THF (75 mL) was added $BH_3$·$SMe_2$ (~10.0 M, 3.80 mL). This solution was allowed to stir at rt for 15 h, during which time hyrdogen is evolved. To the catalyst solution was added 5-(2-chloroacetyl)-2-(2,5-dimethylpyrrol-1-yl)-pyridine (5.5134 g, 22.168 mmol), in THF (10 mL) via syringe pump over 3 h. After an additional 3 h, the reaction was quenched by the slow addition of water (15 mL ), causing slow hydrogen evolution. After 1 h from water addition, the reaction solution was added to diisopropylether (50 mL), EtOAc (50 mL), and 2N HCl (200 mL) and stirred well for 15 min. The phases were separated and the aqueous phase extracted with EtOAc (150 mL). The combined organic phases were further extracted with brine (125 mL) containing 12.5 M NaOH soln (1.5 mL). The solution was dried ($MgSO_4$), filtered and concentrated to provide 5.27 g (95%) of crude product Chiral HPLC (Chiracel OG column, Daicel Corporation, with UV detection) showed this material to be a 91.8:8.2 mixture of desired (R) to undesired (S) enantiomers. The crude was crystallized from EtOAc/hexanes providing two crops of material, totalling 3.7098 g (67%) of pure material that was a 97.5:2.5 mixture of enantiomers.

$^1$H NMR (400 MHz, $CDCl_3$): 2.12 (s, 6), 2.85 (d, 1, J=3.4), 3.7 (dd, 1, J=8.6, 11.3), 3.83 (dd, 1, J=3.6, 11.3), 5.02 (ddd, 1, J=3.4, 3.4, 8.3), 5.89 (s, 2), 7.23 (d, 1, J=9.2), 7.88 (dd, 1, J=2.6, 8.3), 8.60 (d, 1, J=2.4). $^{13}$C NMR (100 MHz, CDCl$_{13}$): 13.11, 50.00, 71.06, 107.16, 121.92, 128.68, 135.18, 136.37, 147.34, 151.65. AP+=251.1.

EXAMPLE 7

N-methyl (4-(2-(2-(6-(2,5 dimethylpyrrol-1-yl) pyridin-3-yl)2(R)-hydroxyethylamino)ethoxy)phen-1-yl)acetate

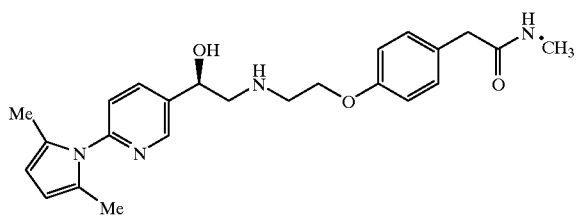

To a solution of compound produced as in Example 6 (9.99 g, 39.8 mmol) in DMSO (80 mL) was added methyl 4-(2-aminoethoxy)phenylacetamide (16.23 g, 77.93 mmol) followed by KOt-Bu (4.49 g, 40.0 mmol). The mixture was heated in an 80° C. bath for 20 h. After cooling, the mixture was added to water (300 mL) and EtOAc (300 mL). The phases were separated and the organic layer further extracted with water (2×200 mL). The organic phase was extracted with brine, dried (K$_2$CO$_3$), filtered and concentrated to provide 13.93 g (83%) of title compound as a hard yellow solid.

$^1$H NMR (300 MHz, CDCl$_3$): 2.14 (s, 6), 2.77 (d, 3, J=4.8), 2.84 (dd, 1, J=9.5, 12.2), 3.07-3.21 (m, 3), 3.54 (s, 2), 4.13 (t, 2, J=5.0), 4.84 (dd, 1, J=3.3, 9.3), 5.47 (br s, 1), 5.92 (s, 2), 6.93 (d, 2, J=8.7), 7.20 (d, 2, J=8.7), 7.24 (d, 1, J=8.1), 7.91 (dd, 1, J=2.3, 8.1), 8.60 (d, 1, J=2.2). $^{13}$C NMR (100 MHz, CDCl$_3$): 13.15, 26.46, .42.70,48.34, 56.69, 67.36, 69.37, 106.87, 114.96, 121.67, 127.34, 128.59, 130.67, 135.76, 136.68, 147.22, 151.36, 157.96, 172.06. Anal. Calcd for C$_{24}$H$_{30}$N$_4$O$_3$: C, 68.22; H, 7.16; N, 13.26. Found: C, 67.82; H, 7.39; N, 13.03.

Preparation 1

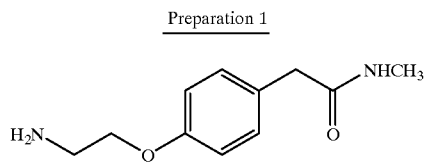

Methyl 4-(2-aminoethoxy)phenylacetamide

Methyl 4–2-(N-benzyloxycarbonylamino)ethoxy) phenylacetamide (1 8.4 kg, 53.73 mol) and 1.84 kg 10% palladium on carbon (50% H$_2$O wet) were suspended in 276 L of methanol under nitrogen, and the reaction vessel pressurized to 50 psig with hydrogen gas. This H$_2$ pressure was maintained by additional charges of H$_2$until there was no further uptake of H$_2$(approx. 20 hours) and the reaction was complete by thin layer chromatography. After purging the vessel with N$_2$, the mixture was heated to 45° C. and filtered at this temperature through Celite®. The solvent was displaced with toluene until a final volume of 30 L was achieved. After cooling to 5° C. the resulting solids were filtered off, washed with cold toluene, and vacuum dried to give the title compound (9.95 kg, 88.9% of theory). NMR (300 MHz, d$_6$-DMSO): δ=7.99–7.57 (m; 1H), 7.20–7.10(d, 2H), 6.90–6.80 (d, 2H), 3.93–3.83 (m, 2H), 3.30 (s, 2H), 3.00–2.62(m, 4H), 2.57 (d, 2H).

What is claimed is:

1. A compound having the formula

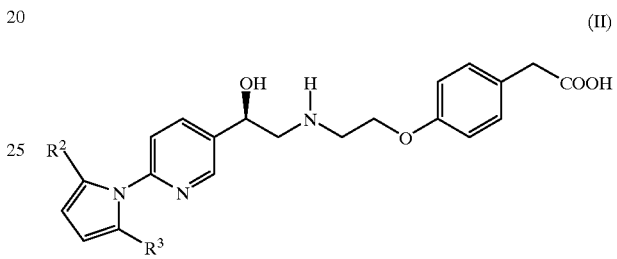

(II)

wherein R$^2$ and R$^3$ are independently C$_1$–C$_3$ alkyl or phenyl.

2. A compound having the formula

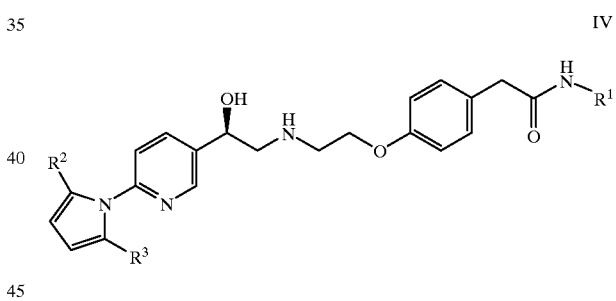

IV wherein R$^1$ is C$_1$–C$_8$ alkyl, and R$^2$ and R$^3$ are independently C$_1$–C$_3$ alkyl or phenyl.

* * * * *